(12) United States Patent
Brand (10) Patent No.: US 10,485,941 B2
(45) Date of Patent: Nov. 26, 2019

(54) SYSTEM FOR ENHANCING SECRETION REMOVAL FROM AN AIRWAY OF A SUBJECT

(71) Applicant: KONINKLIJKE PHILIPS N.V., Eindhoven (NL)

(72) Inventor: Maarten Leonardus Christian Brand, Murrysville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 600 days.

(21) Appl. No.: 14/442,147

(22) PCT Filed: Nov. 8, 2013

(86) PCT No.: PCT/IB2013/060006
§ 371 (c)(1),
(2) Date: May 12, 2015

(87) PCT Pub. No.: WO2014/076618
PCT Pub. Date: May 22, 2014

(65) Prior Publication Data
US 2016/0287823 A1 Oct. 6, 2016

Related U.S. Application Data

(60) Provisional application No. 61/727,779, filed on Nov. 19, 2012.

(51) Int. Cl.
*A61M 16/00* (2006.01)
*A61M 16/16* (2006.01)
(Continued)

(52) U.S. Cl.
CPC .... *A61M 16/0009* (2014.02); *A61M 16/0057* (2013.01); *A61M 16/0066* (2013.01);
(Continued)

(58) Field of Classification Search
CPC .............. A61M 16/00; A61M 16/0003; A61M 2205/52; A61M 2230/005;
(Continued)

(56) References Cited

U.S. PATENT DOCUMENTS 6,584,973 B1 7/2003 Biondi
8,051,854 B2 11/2011 Faram
(Continued)

FOREIGN PATENT DOCUMENTS

CN 1849150 A 10/2006
CN 200960346 Y 10/2007
(Continued)

*Primary Examiner* — Steven O Douglas
(74) *Attorney, Agent, or Firm* — Michael W. Haas (57) ABSTRACT

A system for enhancing secretion removal from an airway of a subject by applying a negative pressure to the airway of the subject just prior to an exsufflation is provided. The negative pressure is applied just after the subject has inhaled under his own power and/or just after generator mechanical insufflation by the system. The negative pressure applied just after inhalation/insufflation and just prior to exsufflation temporarily reduces the cross-sectional area of the airway of the subject. A reduced cross-sectional area User of the airway increases the velocity of air through the airway during a subsequent exsufflation, which results in enhanced secretion clearance. In some embodiments, the system includes one or more of a pressure generator, a subject interface, one or more sensors, a user control interface, one or more processors, and/or other components.

21 Claims, 4 Drawing Sheets

(51) Int. Cl.
*A61M 16/06* (2006.01)
*A61M 16/08* (2006.01)
*A61M 16/20* (2006.01)
*A61M 16/10* (2006.01)

(52) U.S. Cl.
CPC .... *A61M 16/0072* (2013.01); *A61M 16/0075* (2013.01); *A61M 16/024* (2017.08); *A61M 16/0666* (2013.01); *A61M 16/0875* (2013.01); *A61M 16/161* (2014.02); *A61M 16/20* (2013.01); *A61M 2016/003* (2013.01); *A61M 2016/0027* (2013.01); *A61M 2016/0036* (2013.01); *A61M 2016/102* (2013.01); *A61M 2205/3331* (2013.01); *A61M 2205/3365* (2013.01); *A61M 2205/3368* (2013.01); *A61M 2205/502* (2013.01); *A61M 2230/42* (2013.01)

(58) Field of Classification Search
CPC ...... A61M 2230/42; A61M 2016/0018; A61M 16/0009; A61M 16/161; A61M 16/024; A61M 16/0057; A61M 16/0066; A61M 16/0072; A61M 16/0075; A61M 16/0666; A61M 16/0875; A61M 16/20; A61M 2016/0027; A61M 2016/003; A61M 2016/0036; A61M 2016/102; A61M 2205/3331; A61M 2205/3365; A61M 2205/3368; A61M 2205/502
See application file for complete search history.

(56) References Cited

U.S. PATENT DOCUMENTS

| | | | |
|---|---|---|---|
| 2003/0051729 A1* | 3/2003 | Be'eri | A61M 16/20 |
| | | | 128/204.18 |
| 2005/0051174 A1 | 3/2005 | Emerson | |
| 2007/0186928 A1* | 8/2007 | Be'Eri | A61M 16/00 |
| | | | 128/204.18 |
| 2011/0220107 A1 | 9/2011 | Kimm | |
| 2011/0221427 A1 | 9/2011 | Ovsyanko | |
| 2012/0103337 A1 | 5/2012 | Avni | |
| 2012/0111329 A1 | 5/2012 | Brand | |
| 2012/0199127 A1* | 8/2012 | Garde | A61M 16/00 |
| | | | 128/204.23 |
| 2014/0116441 A1* | 5/2014 | McDaniel | A61M 16/0051 |
| | | | 128/204.23 |
| 2016/0228660 A1* | 8/2016 | Lee | A61B 5/087 |

FOREIGN PATENT DOCUMENTS

| | | |
|---|---|---|
| CN | 102216780 A | 10/2011 |
| CN | 102264423 A | 11/2011 |
| CN | 102441211 A | 5/2012 |
| CN | 102458544 A | 5/2012 |
| WO | WO2007054829 A2 | 5/2007 |
| WO | WO2010046874 A2 | 4/2010 |
| WO | WO2010058308 A2 | 5/2010 |
| WO | WO2010071919 A1 | 7/2010 |
| WO | WO2011045735 A1 | 4/2011 |
| WO | WO212085792 A2 | 6/2012 |
| WO | WO2012085787 A2 | 6/2012 |

* cited by examiner

SYSTEM FOR ENHANCING SECRETION REMOVAL FROM AN AIRWAY OF A SUBJECT

CROSS-REFERENCE TO RELATED APPLICATIONS

This patent application claims the priority benefit under 35 U.S.C. § 371 of international patent application no. PCT/IB2013/060006, filed Nov. 8, 2013, which claims the priority benefit under 35 U.S.C. § 119(e) of U.S. Provisional Application No. 61/727,779, filed on Nov. 19, 2012, the contents of which are herein incorporated by reference.

BACKGROUND OF THE INVENTION

1. Field of the Invention

The present invention pertains to a system and method for enhancing secretion removal from an airway of a subject by applying a negative pressure to the airway of the subject just prior to an exsufflation.

2. Description of the Related Art

Various systems for increasing patient cough flow through exsufflation are known. Conventional mechanical inexsufflation (MI-E) is generally accomplished by delivering a positive pressure during an inhalation of a subject and delivering a negative pressure during an exhalation. The pressure level during inhalation may be sufficiently high that the lungs of the subject are at least partially filled during insufflation. After insufflation, the pressure may be reduced with sufficient abruptness that expiratory flow through the airway of the subject is sufficient to remove mucus and/or other debris from the airway and/or lungs of the subject during exsufflation. Secretions built up in the airway of the subject over time may be expelled with the gas.

SUMMARY OF THE INVENTION

Accordingly, one or more aspects of the present disclosure relate to a device configured to enhance secretion removal from an airway of a subject. The system comprises a pressure generator and one or more processors. The pressure generator is configured to generate a pressurized flow of breathable gas for delivery to the airway of the subject. The one or more processors are configured to execute computer program modules. The computer program modules comprise a control module. The control module is configured to control the pressure generator to maintain a pressure level of the pressurized flow of breathable gas below ambient air pressure just prior to an exsufflation.

Yet another aspect of the present disclosure relates to a method of enhancing secretion removal from an airway of a subject with a secretion removal system. The system comprises a pressure generator and one or more processors. The one or more processors are configured to execute computer program modules. The computer program modules include a control module. The method comprises generating a pressurized flow of breathable gas for delivery to the airway of the subject with the pressure generator; and controlling the pressure generator with the control module to maintain a pressure level of the pressurized flow of breathable gas below ambient air pressure just prior to an exsufflation.

Still another aspect of present disclosure relates to a system for enhancing secretion removal from an airway of a subject. The system comprises means for generating a pressurized flow of breathable gas for delivery to the airway of the subject; and means for executing computer program modules. The computer program modules comprising means for controlling the means for generating the pressurized flow of breathable gas to maintain a pressure level of the pressurized flow of breathable gas below ambient air pressure just prior to an exsufflation.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
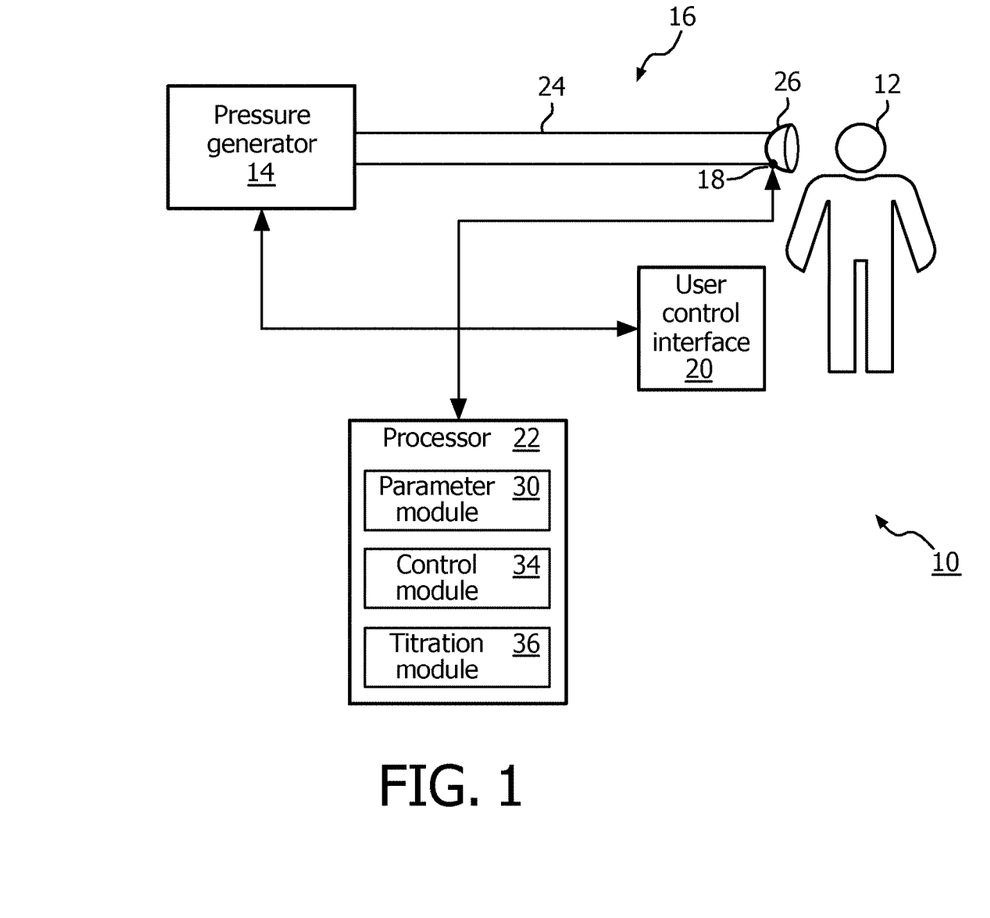
FIG. 1 is a schematic illustration of a system configured to enhance secretion removal from an airway of a subject.

FIG. 1 schematically illustrates an exemplary embodiment of a system 10 configured to enhance secretion removal from an airway of a subject 12. System 10 is configured to enhance secretion removal by applying a negative pressure to the airway of subject 12 just prior to an exsufflation. The negative pressure may be applied just after subject 12 has inhaled under his own power and/or just after mechanical insufflation by system 10. The negative pressure applied just after inhalation/insufflation and just prior to exsufflation may temporarily reduce the cross-sectional area of the airway of subject 12. A reduced cross-sectional area of the airway may increase the velocity of air through the airway during a subsequent exsufflation. The increased velocity of air through the airway may result in enhanced secretion clearance. In some embodiments, system 10 includes one or more of a pressure generator 14, a subject interface 16, one or more sensors 18, a user control interface 20, one or more processors 22, and/or other components.

Pressure generator 14 is configured to generate a pressurized flow of breathable gas for delivery to the airway of a subject. Pressure generator 14 is configured to deliver the pressurized flow of gas via subject interface 16, and/or other devices. Pressure generator 14 may be configured to receive a flow of gas from a gas source, such as the ambient atmosphere, and elevate and/or reduce the pressure of that gas for delivery to subject 12. Pressure generator 14 may control one or more parameters of the pressurized flow of breathable gas (e.g., flow rate, pressure, volume, velocity, humidity, temperature, composition) for therapeutic purposes, or for other purposes. Pressure generator 14 is any device, and/or combination of devices, such as, for example, a pump, one or move valves, a blower, a piston, or bellows, that is capable of elevating and/or reducing the pressure of the received gas for delivery to subject 12. The present disclosure contemplates that gas other than ambient atmospheric air may be introduced into system 10 for delivery to the patient. In some embodiments, system 10 is a dedicated exsufflation device. In some embodiments, system 10 may be configured for insufflation and/or exsufflation (e.g., inexsufflation), and/or other therapeutic regimes.

By way of a non-limiting example, pressure generator 14 may be controlled by processor 22 to adjust the parameters of the pressurized flow of breathable gas in accordance with an exsufflation therapy regime. In some embodiments, the therapy regime may dictate that the pressurized flow of breathable gas is delivered to the airway of subject 12 at a first negative pressure level just prior to exsufflation to reduce the cross-sectional area of the airway of subject 12. After generating the pressurized flow of breathable gas for delivery to the airway of subject 12 at the first negative pressure level just prior to exsufflation, pressure generator 14 may be controlled to generate the pressurized flow of breathable gas for delivery to the airway of subject 12 at a second negative pressure level during exsufflation. In some embodiments, the pressure level may be decreased from the first negative pressure level to the second negative pressure level (e.g., the pressure may be decreased from −30 cmH$_2$O to −40 cmH$_2$O). In some embodiments, pressure generator 14 may be controlled to adjust the first negative pressure just prior to exsufflation to make it easier for subject 12 to hold their breath prior to the exsufflation.

The pressurized flow of breathable gas is delivered to the airway of subject 12 via subject interface 16. Subject interface 16 is configured to communicate the pressurized flow of breathable gas generated by pressure generator 14 to the airway of subject 12. As such, subject interface 16 comprises a conduit 24, an interface appliance 26, and/or other components. Conduit 24 is configured to convey the pressurized flow of breathable gas to interface appliance 26. Conduit 24 may be a flexible tube and/or other device configured to convey the pressurized flow of breathable gas to interface appliance 26. Interface appliance 26 is configured to deliver the pressurized flow of breathable gas to the airway of subject 12. In some embodiments, subject interface 16 is non-invasive. As such, interface appliance 26 non-invasively engages subject 12. Non-invasive engagement includes removably engaging an area (or areas) surrounding one or more external orifices of the airway of subject 12 (e.g., nostrils and/or mouth) to communicate gas between the airway of subject 12 and subject interface 16. Some examples of non-invasive interface appliance 26 may include, for example, a blow tube, a nasal cannula, a nasal mask, a nasal/oral mask, a full face mask, a total face mask, or other interface appliances that communicate a flow of gas with an airway of a subject. The present disclosure is not limited to these examples, and contemplates delivery of the pressurized flow of breathable gas to subject 12 using any subject interface.

One or more sensors 18 are configured to generate one or more output signals conveying information related to one or more parameters of the pressurized flow of breathable gas. The one or more parameters may include, for example, one or more of a flow rate, a volume, a pressure, a composition (e.g., concentration(s) of one or more constituents), humidity, temperature, acceleration, velocity, a respiration rate, timing, and/or other gas parameters. Sensors 18 may include one or more sensors that measure such parameters directly (e.g., through fluid communication with the pressurized flow of breathable gas at pressure generator 14 or in subject interface 16). Sensors 18 may include one or more sensors that generate output signals related to one or more parameters of the pressurized flow of breathable gas indirectly. For example, one or more of sensors 18 may generate an output based on an operating parameter of pressure generator 14 (e.g., a motor current, voltage, rotational velocity, and/or other operating parameters), and/or other sensors. Although sensors 18 are illustrated at a single location in subject interface 16, this is not intended to be limiting. Sensors 18 may include sensors disposed in a plurality of locations, such as for example, within pressure generator 14, within (or in communication with) conduit 24, within (or in communication with) interface appliance 26, and/or other locations.

User control interface 20 is configured to provide an interface between system 10 and subject 12 through which subject 12 provides information to and receives information from system 10. This enables data, results, and/or instructions and any other communicable items, collectively referred to as "information," to be communicated between subject 12 and processor 22, and/or any other component of system 10. In some embodiments, user control interface 20 may be configured such that information indicating whether subject 12 is ready for exsufflation comprises an input by subject 12 to user control interface 20. Examples of interface devices suitable for inclusion in user control interface 20 include a keypad, buttons, switches, a keyboard, knobs, levers, a display screen, a touch screen, speakers, a microphone, an indicator light, an audible alarm, a printer, a tactile feedback device, a gesture recognition device, and/or other interface devices. For example, in some embodiments subject 12 pushes a button to communicate to processor 22 that subject 12 is ready for exsufflation. In some embodiments, user control interface 20 includes a plurality of separate interfaces. For example, system 10 may be configured with the push button mentioned above, and/or a gesture (e.g.; facial movement such as blinking) recognition device for use by a subject who may not have full physical control of their extremities (e.g., a fully or partially paralyzed subject).

It is to be understood that other communication techniques, either hard-wired or wireless, are also contemplated by the present disclosure as user control interface 20. For example, the present disclosure contemplates that user control interface 20 is a remote control. In this example, information indicating that subject 12 is ready for exsufflation is wirelessly transmitted to processor 22. Other exemplary input devices and techniques adapted for use with system 10 as user control interface 20 include, but are not limited to, an RS-232 port, RF link, an IR link, modem (telephone, cable or other). In short, any technique for communicating information with system 10 is contemplated by the present disclosure as user control interface 20.

Processor 22 is configured to provide information processing capabilities in system 10. As such, processor 22 may include one or more of a digital processor, an analog processor, a digital circuit designed to process information, an analog circuit designed to process information, a state machine, and/or other mechanisms for electronically processing information. Although processor 22 is shown in FIG. 1 as a single entity, this is for illustrative purposes only. In some embodiments, processor 22 includes a plurality of processing units. These processing units may be physically located within the same device, or processor 22 may represent processing functionality of a plurality of devices operating in coordination. In some embodiments, communication between processors 22 and/or sensor(s) 18 occurs wirelessly or via wires.

As shown in FIG. 1, processor 22 may be configured to execute one or more computer program modules. The one or more computer program modules comprise one or more of a parameter module 30, a control module 34, a titration module 36, and/or other modules. Processor 22 may be configured to execute modules, 30, 34 and/or 36 by software; hardware; firmware; some combination of software, hardware, and/or firmware; and/or other mechanisms for configuring processing capabilities on processor 22.

It should be appreciated that although modules 30, 34, and 36 are illustrated in FIG. 1 as being co-located within a single processing unit, in embodiments in which processor 22 includes multiple processing units, one or more of modules 30, 34, and/or 36 may be located remotely from the other modules. The description of the functionality provided by the different modules 30, 34, and/or 36 described below is for illustrative purposes, and is not intended to be limiting, as any of modules 30, 34, and/or 36 may provide more or less functionality than is described. For example, one or more of modules 30, 34, and/or 36 may be eliminated, and some or all of its functionality may be provided by other ones of modules 30, 34, and/or 36. As another example, processor 22 may be configured to execute one or more additional modules that may perform some or all of the functionality attributed below to one of modules 30, 34, and/or 36.

Parameter module 30 is configured to determine one or more parameters of the pressurized flow of breathable gas. The one or more parameters of the pressurized flow of breathable gas may comprise gas parameters related to the pressurized flow of breathable gas, breathing parameters related to respiration of subject 12, and/or other parameters. The one or more parameters may include, for example, one or more of a flow rate, a volume, a pressure, a composition (e.g., concentration(s) of one or more constituents), humidity, temperature, acceleration, velocity, a respiration rate, a timing, and/or other gas parameters. Parameter module 30 is configured to determine the one or more parameters based on the output signals of sensors 18. The information determined by parameter module 30 may be used by control module 34 to control pressure generator 14, and/or for other uses. For example, the output signals from sensors 18 may convey information related to a volume of gas expired by subject 12 while the pressurized flow of breathable gas is at a negative pressure level before the exsufflation.

Parameter module 30 may be configured to determine the volume of gas expired by subject 12, the length of time the pressurized flow of breathable gas is at the negative pressure level, and/or other parameters. As another example, parameter module 30 may be configured to detect completion of a preparatory inhalation based on the output signals. A preparatory inhalation may comprise an inhalation by subject 12 prior to an exsufflation. Detecting completion of a preparatory inhalation may comprise determining one or more parameters of the pressurized flow of breathable gas. The one or more parameters may include a preparatory inhalation tidal volume, a tidal flow rate, and/or other parameters. The preparatory inhalation tidal volume may comprise a tidal volume of air that is more than a normal and/or average volume of air inhaled by subject 12 prior to an exsufflation. The tidal flow rate may be determined to be substantially zero at an end of the preparatory inhalation.

Control module 34 is configured to control pressure generator 14 to adjust one or more parameters of the pressurized flow of breathable gas. The one or more parameters may include pressure, among other things. Control module 34 may control pressure generator 14 to maintain a pressure level of the pressurized flow of breathable gas below ambient air pressure just prior to an exsufflation (e.g., negative pressure). In some embodiments, control module 34 may control pressure generator 14 to maintain a pressure level of the pressurized flow of breathable gas below zero just prior to an exsufflation. The pressure level may be determined at manufacture, determined by control module 34 based on information entered by subject 12 and/or other users (e.g., a caregiver, a doctor) via user control interface 20, determined by control module 34 based on previous respiration of subject 12, and/or determined by other methods. The pressure level may be between 0 cmH$_2$O and about −50 cmH$_2$O. In some embodiments, the pressure level may be about −40 cmH$_2$O.

In some embodiments, control module 34 may be configured to begin maintaining the pressure at the negative pressure level described above (the first negative pressure level) automatically. The automatic beginning may be responsive to parameter information determined by parameter module 30 indicating inhalation and/or insufflation of subject 12 has ceased.

For example, a normal tidal breathing volume for an inhalation of subject 12 may be determined by parameter module 30. The normal tidal breathing volume may be determined based on information conveyed by output signals from sensors 18. The normal tidal breathing volume may include an average tidal breathing volume determined over a series of breaths. An instance of an increased tidal breathing volume above the normal tidal breathing volume (e.g., by a predetermined amount) during an inhalation may be detected by parameter module 30. The instance of the increased tidal breathing volume may indicate a preparatory inhalation. The instance of the increased tidal breathing volume (e.g., the preparatory inhalation) may be detected responsive to the tidal breathing volume breaching a threshold level. After determining an instance of increased tidal breathing volume, parameter module 30 may be configured to determine when the tidal flow rate is substantially zero (e.g., no flow into and/or out of an airway of the subject). In some embodiments, the substantially zero flow rate may indicate that subject 12 has finished inhaling, is holding their breath, and is ready to cough, for example.

Responsive to the determination that subject 12 has finished inhaling (e.g., the preparatory inhalation is complete), pressure generator 14 may be controlled by control module 34 to begin generating a negative pressure for delivery to the airway of subject 12. Pressure generator 14 may be configured to begin generation of the negative pressure (e.g., the first negative pressure) responsive to the determination that the tidal flow rate is substantially zero. Pressure generator 14 may be controlled with control module 34 to cease generating the negative pressure for delivery to the airway of subject 12 responsive to parameter module 30 determining that the first negative pressure level has been reached in the airway of subject 12. Subject 12 may cough, for example, responsive to the negative pressure ceasing. In some embodiments, control module 34 may be configured to control user control interface 20, for example, to indicate to subject 12 that the negative pressure has ceased.

In some embodiments, control module 34 may be configured to begin maintaining the pressure at the first negative pressure level responsive to receiving information via user control interface 20 indicating that subject 12 is ready for exsufflation. Subject 12 may indicate exsufflation readiness via user control interface 20, and/or by another method. User control interface 20 may be configured to transmit information conveying exsufflation readiness of subject 12 to control module 34.

Control module 34 may be configured to control pressure generator 14 to maintain the pressurized flow of breathable gas at the first negative pressure level for a predetermined amount of time, until a volume of gas expired by the subject before exsufflation breaches a threshold volume, responsive to control inputs by subject 12 to user control interface 20, until the generated pressure breaches a threshold level, and/or responsive to other conditions. The predetermined amount of time and/or the expired gas volume threshold may be determined at manufacture, determined by control module 34 based on information entered by subject 12 and/or other users (e.g., a caregiver, a doctor) via user control interface 20, determined by control module 34 based on previous respiration of subject 12, and/or determined by another method.

For example, control module 34 may control pressure generator 14 to control the pressurized flow of breathable gas at a first negative pressure level of −40 $cmH_2O$. Control module 34 may be configured to control pressure generator 14 to control the pressurized flow of breathable gas at the first pressure level until a volume of gas expired by subject 12 breaches a threshold level before the exsufflation. The expired gas volume threshold may be configured such that the expired gas volume breaching the threshold level indicates that subject 12 in unable to hold their breath when the −40 $cmH_2O$ pressure is applied to the airway of subject 12. The expired gas volume breaching the threshold level may indicate that the first negative pressure level should be adjusted.

Titration module 36 is configured to adjust the first negative pressure level based on the output signals generated by sensors 18, parameter information determined by parameter module 30, and/or based on other information. Titration module 36 is configured to adjust the first negative pressure level to enhance secretion removal during exsufflation. In some embodiments, titration module 36 may be configured to adjust the first negative pressure level responsive to the volume of gas expired by subject 12 breaching a threshold level before the exsufflation. In some embodiments, titration module 36 may be configured to adjust the first negative pressure level based on achieved cough flow (e.g., maximum expiratory flow). In some embodiments, control module 34 may be configured to control pressure generator 14 to maintain the first negative pressure level for subsequent breathing cycles based on the adjustment(s) made by titration module 36.

Continuing with the example above, control module 34 may control pressure generator 14 to control the pressurized flow of breathable gas at the first negative pressure level of −40 $cmH_2O$. Responsive to the volume of gas expired by subject 12 breaching a threshold level before the exsufflation, titration module 36 may be configured to cause pressure generator 14 to maintain the first negative pressure at an adjusted pressure of −30 $cmH_2O$. The −30 $cmH_2O$ pressure level is closer to zero and may make it easier for subject 12 to hold their breath. In some embodiments, control module 34 may be configured to control pressure generator 14 to maintain the first negative pressure level at −30 $cmH_2O$ for subsequent breathing cycles based on the adjustment made by titration module 36.

In some embodiments, control module 34 may be configured to control pressure generator 14 to maintain the pressure level of the pressurized flow of breathable gas at the first negative pressure level just prior to exsufflation and at a second negative pressure level during exsufflation. Control module 34 may be configured to control pressure generator 14 to maintain the pressure level of the pressurized flow of breathable gas at the first negative pressure level just prior to exsufflation and at the second negative pressure level during exsufflation responsive to receiving information conveying an indication that subject 12 is ready for exsufflation. Control module 34 may be configured to control pressure generator 14 to maintain the pressure level of the pressurized flow of breathable gas at the second pressure level responsive to a pre-determined amount of time at the first pressure level expiring, and/or responsive to other conditions.

In some embodiments, the pressure level may be decreased from the first negative pressure level to the second negative pressure level (e.g., the pressure may be decreased from −30 $cmH_2O$ to −40 $cmH_2O$). In some embodiments, during exhalation, pressure generator 14 may be controlled to hold the pressure level of the second negative pressure constant. In some embodiments, titration module 36 may be configured to control pressure generator 14 to adjust the pressure level of the second negative pressure to one or more other negative pressure levels during exhalation.

In some embodiments, control module 34 may be configured to control user control interface 20 and/or other devices to signal subject 12 when the pressure maintained at the first pressure level ceases, and/or is about to cease (e.g., after maintaining the pressure at the first pressure level and before maintaining the pressure at the second pressure level). In some embodiments, the second negative pressure level may not be applied. Subject 12 may be signaled and allowed to cough naturally after applying pressure at the first negative pressure level.

By way of a non-limiting example, pressure generator 14 may be controlled by control module 34 to adjust the parameters of the pressurized flow of breathable gas in accordance with an exsufflation therapy regime. In some embodiments, the therapy regime may dictate that the pressurized flow of breathable gas is delivered to the airway of subject 12 at the first negative pressure level just prior to exsufflation and at the second negative pressure level during exsufflation. Control module 34 may be configured to begin maintaining the pressure at the first negative pressure level responsive to parameter information (e.g., determined by parameter module 30) indicating an inhalation of subject 12 has ceased. After expiration of a predetermined amount of time at the first negative pressure level, pressure generator 14 may be controlled to generate the pressurized flow of breathable gas for delivery to the airway of subject 12 at the second negative pressure level during exsufflation.

Figure 2:
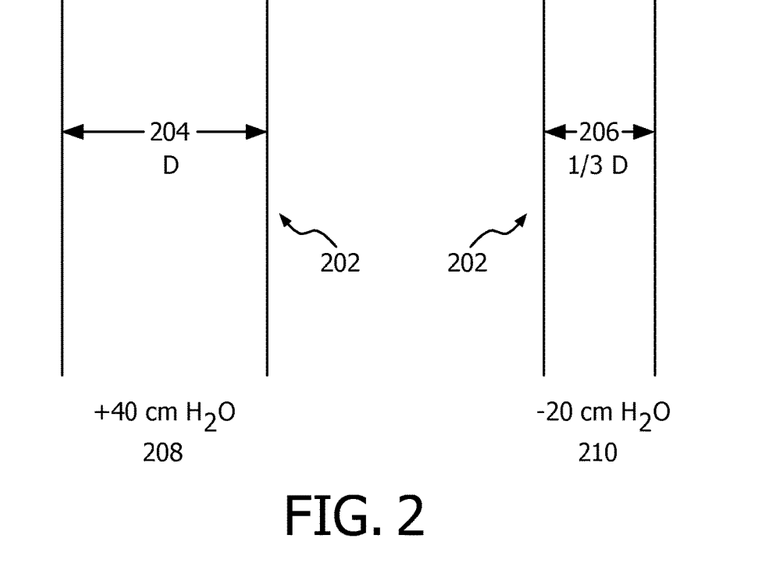
FIG. 2 is an illustration of an airway at two different diameters just prior to a normal exsufflation.

FIG. 2 is an illustration of an airway 202 at two different diameters 204, 206, just prior to a normal exsufflation. Diameter 204 represents the typical diameter of airway 202 just prior to an exsufflation. Diameter 206 represents the diameter of airway 202 just prior to an exsufflation with an applied negative pressure. The negative pressure applied just after inhalation/insufflation and just prior to exsufflation may temporarily reduce the diameter of airway 202. Reducing the diameter of airway 202 may increase the velocity of air through airway 202 during a subsequent exsufflation. The increased velocity of air through airway 202 may result in enhanced secretion clearance. In FIG. 2, airway 202 is illustrated just prior to an exsufflation at an example pressure 208 of +40 $cmH_2O$. Airway 202 is illustrated with an applied negative pressure at an example pressure 210 of −20 $cmH_2O$. The example pressures are not intended to be limiting. Typical diameter 204 of airway 202 just prior to an exsufflation is shown at a diameter of "D". Diameter 206 of airway 202 with an applied negative pressure 210 is shown at a diameter of "⅓ D".

Figure 3:
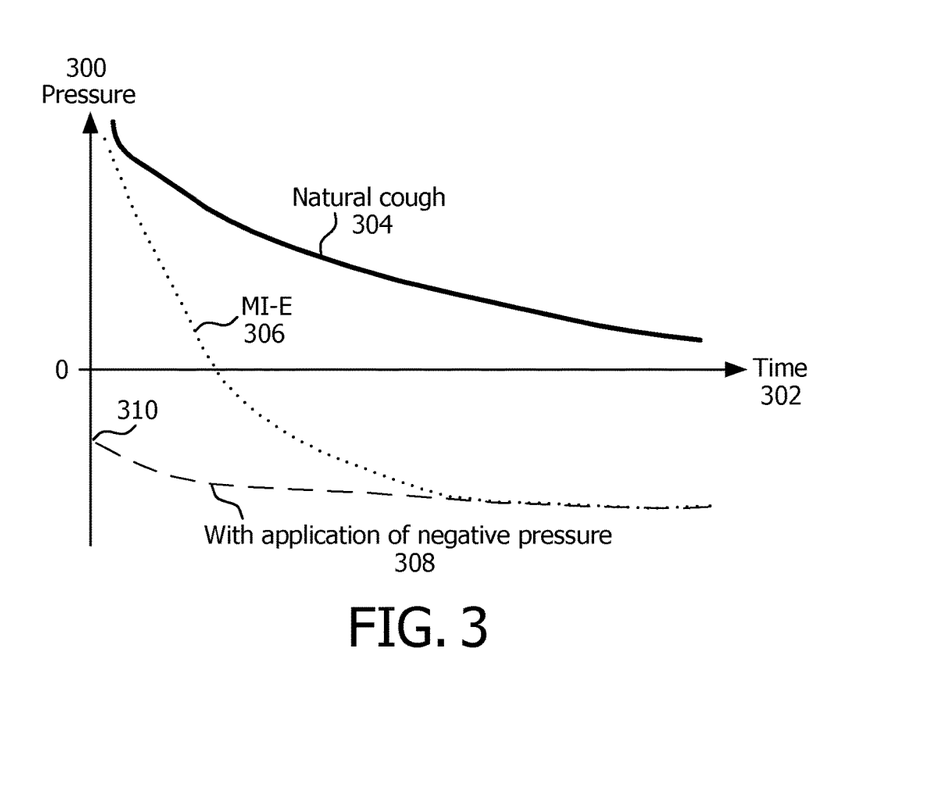
FIG. 3 illustrates pressure as a function of time during an expiratory phase of a breathing cycle.

FIG. 3 illustrates pressure 300 as a function of time 302 during an expiratory phase of a breathing cycle. Line 304 represents pressure as a function of time for a natural cough. Line 306 represents pressure as a function of time for typical mechanical inexsufflation. Line 308 represents pressure as a function of time after applying negative pressure (as described above with respect to FIG. 1) before the onset of an exsufflation. Line 308 is the only line of the three that has a starting point 310 at a pressure that is below zero.

Figure 4:
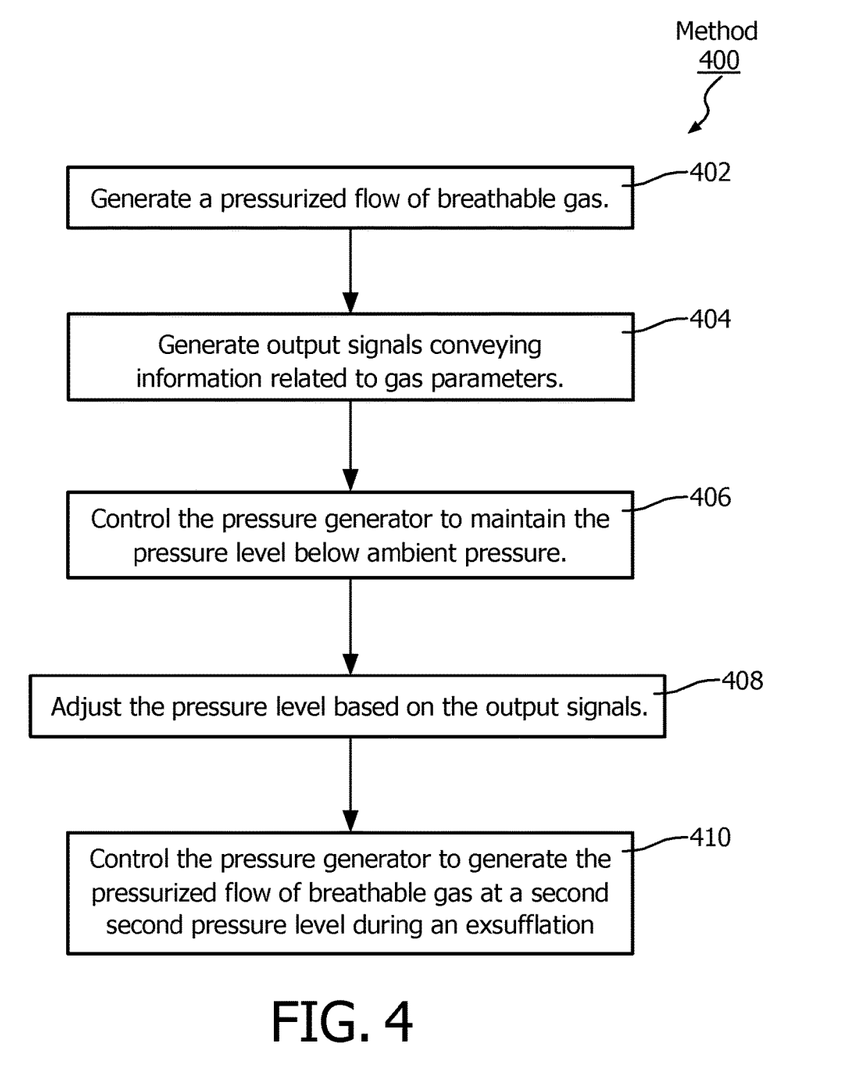
FIG. 4 illustrates a method to enhance secretion removal from an airway of a subject.
Figure 5:
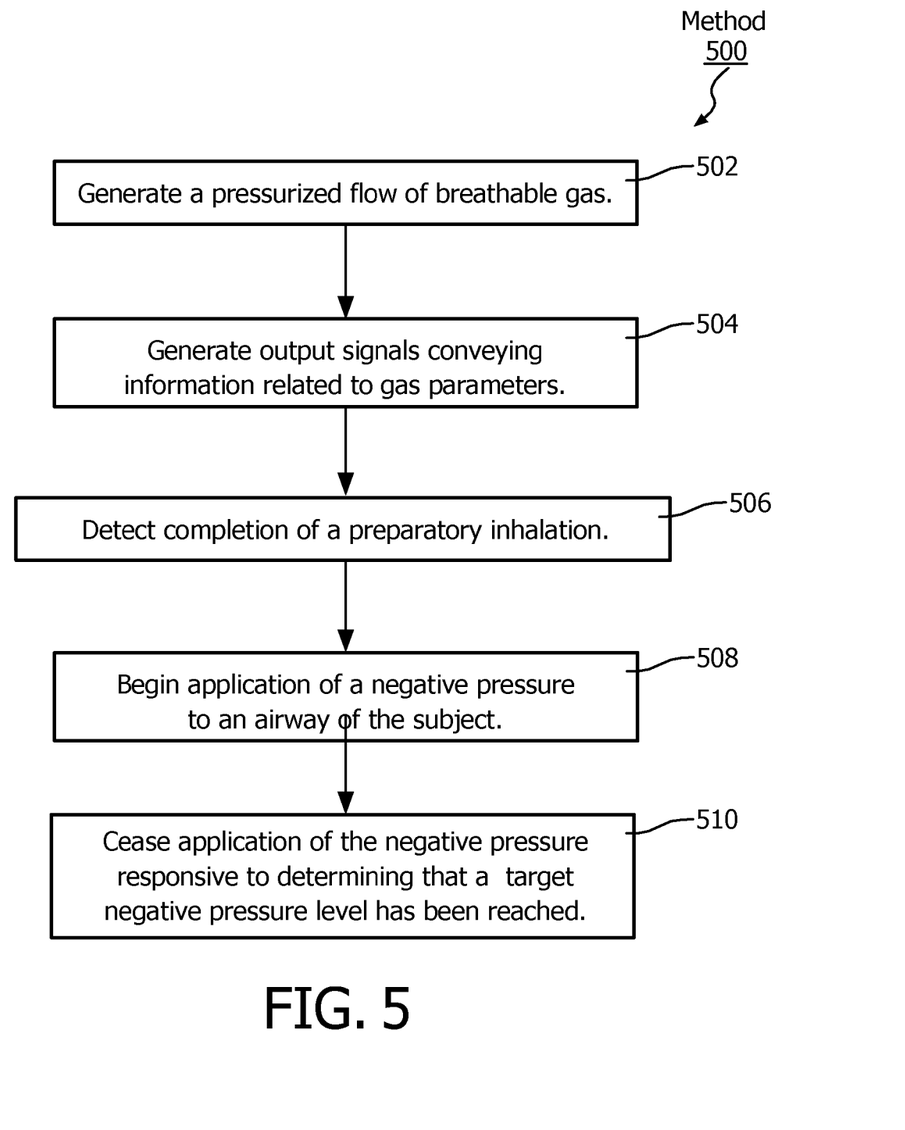
FIG. 5 illustrates another method to enhance secretion removal from an airway of a subject.

FIG. 4 and FIG. 5 illustrate method 400 and method 500 to enhance secretion removal from an airway of a subject with a secretion removal enhancement system. The system comprises a pressure generator, one or more processors, and a user control interface. The one or more processors are configured to execute computer program modules. The computer program modules include a control module and a titration module. The operations of methods 400 and/or 500 presented below are intended to be illustrative. In some embodiments, methods 400 and/or 500 may be accomplished with one or more additional operations not described, and/or without one or more of the operations discussed. Additionally, the order in which the operations of methods 400 and/or 500 are illustrated in FIG. 4 and/or in FIG. 5 and described below is not intended to be limiting.

In some embodiments, methods 400 and/or 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of methods 400 and/or 500 in response to instructions stored electronically on an electronic storage medium. The one or more processing devices may include one or more devices configured through hardware, firmware, and/or software to be specifically designed for execution of one or more of the operations of methods 400 and/or 500.

Referring to method 400, at an operation 402, a pressurized flow of breathable gas for delivery to the airway of the subject is generated with the pressure generator. In some embodiments, operation 402 is performed by a pressure generator the same as or similar to pressure generator 14 (shown in FIG. 1 and described herein). At an operation 404, output signals conveying information related to one or more gas parameters of the pressurized flow of breathable gas are generated. In some embodiments, operation 404 is performed by sensors the same as or similar to sensors 18 (shown in FIG. 1 and described herein).

At an operation 406, the pressure generator is controlled with the control module to maintain a pressure level of the pressurized flow of breathable gas below ambient air pressure just prior to an exsufflation. In some embodiments, the pressure generator is controlled to provide the pressurized flow of breathable gas at a first negative pressure level responsive to information received via the user control interface indicating that the subject is ready for exsufflation. In some embodiments, the pressure generator is controlled to provide the pressurized flow of breathable gas at a first negative pressure level based on the output signals (e.g., the output signals may convey information indicating that the subject has finished an inhalation). In some embodiments, operation 406 is performed by a computer program module the same as or similar to control module 34 (shown in FIG. 1 and described herein).

At an operation 408, the first negative pressure level is adjusted with the titration module based on the output signals to enhance secretion removal during the exsufflation. In some embodiments, the output signals convey information related to a volume of gas expired by the subject while the pressurized flow of breathable gas is at the first negative pressure level before the exsufflation. In some embodiments, the first negative pressure level is increased responsive to the volume of gas expired by the subject breaching a threshold level before the exsufflation. In some embodiments, operation 408 is performed by a titration module the same as or similar to titration module 36 (shown in FIG. 1 and described herein).

At an operation 410, the pressure generator is controlled with the control module to generate the pressurized flow of breathable gas at a second negative pressure level for delivery to the airway of the subject during exsufflation. The control module may be configured to control the pressure generator to maintain the pressure level of the pressurized flow of breathable gas at the first negative pressure level just prior to exsufflation and at the second negative pressure level during exsufflation responsive to receiving information conveying an indication that the subject is ready for exsufflation. The control module may be configured to control the pressure generator to maintain the pressure level of the pressurized flow of breathable gas at the second pressure level responsive to a pre-determined amount of time at the first pressure level expiring, and/or responsive to other conditions. In some embodiments, operation 410 is performed by a computer program module the same as or similar to control module 34. In some embodiments, operation 410 is optional.

Referring to method 500, in some embodiments, various operations of method 500 may be automatically (e.g., without the subject and/or other users entering selections and/or providing other input to the system) triggered by the system. The automatic triggering may be based on information determined by a parameter module and/or other components of the system.

At an operation 502, a pressurized flow of breathable gas for delivery to the airway of the subject is generated with the pressure generator. In some embodiments, operation 502 is performed by a pressure generator the same as or similar to pressure generator 14 (shown in FIG. 1 and described herein).

At an operation 504, output signals conveying information related to one or more gas parameters of the pressurized flow of breathable gas are generated. In some embodiments, operation 504 is performed by sensors the same as or similar to sensors 18 (shown in FIG. 1 and described herein).

At an operation 506, completion of a preparatory inhalation is detected. A preparatory inhalation may comprise an inhalation by the subject prior to an exsufflation. Detecting completion of a preparatory inhalation may comprise determining one or more parameters of the pressurized flow of breathable gas. The one or more parameters may include a preparatory inhalation tidal volume, a tidal flow rate, and/or other parameters. The preparatory inhalation tidal volume may comprise a tidal volume of air that is more than a normal and/or average volume of air inhaled by the subject prior to an exsufflation. The tidal flow rate may be determined to be substantially zero at an end of the preparatory inhalation. In some embodiments, the normal tidal breathing volume may be determined based on information conveyed by the output signals from the one or more sensors during normal tidal breathing of the subject over a period of time.

The normal tidal breathing volume may be determined based on output signals related to one or more breaths by the subject. For example, a normal tidal breathing volume may include an average tidal breathing volume over a series of breaths. The normal tidal breathing may be used to set a maximum tidal breathing volume change set point. The preparatory inhalation tidal volume may be detected responsive to the maximum tidal breathing volume breaching a threshold level. For example, the threshold level may be set above the maximum volume change set point by a factor of about 1.3. In some embodiments, the substantially zero flow rate may indicate that the subject has finished inhaling and is ready to cough, for example. In some embodiments, operation 506 is performed by a computer program module the same as or similar to parameter module 30 (shown in FIG. 1 and described herein).

At an operation 508, the pressure generator is controlled to begin generating a negative pressure for delivery to the airway of the subject. The pressure generator may be configured to begin generation of the negative pressure (e.g., a first negative pressure) responsive to the detection of the completion of the preparatory inhalation. In some embodiments, the pressure generator may be configured to begin generation of the negative pressure responsive to the determination that the tidal flow rate is substantially zero. In some embodiments, operation 508 is performed by a computer program module the same as or similar to control module 34 (shown in FIG. 1 and described herein).

At an operation 510, the pressure generator is controlled with the control module to cease generating the negative pressure for delivery to the airway of the subject. The pressure generator may be controlled to cease generating the negative pressure responsive to the parameter module determining that the first negative pressure level has been reached. The subject may cough, for example, responsive to the negative pressure ceasing. In some embodiments, the control module may be configured to control a user control interface, for example, to indicate to the subject that the negative pressure has ceased. In some embodiments, operation 510 is performed by computer program modules the same as or similar to control module 34 and/or parameter module 30 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to enhance secretion removal from an airway of a subject, the system comprising:
    a pressure generator configured to generate a pressurized flow of breathable gas for delivery to the airway of the subject;
    one or more sensors configured to generate output signals conveying information related to one or more gas parameters of the pressurized flow of breathable gas; and
    one or more processors configured to
        detect completion of a preparatory inhalation based on a comparison between the one or more gas parameters associated with the preparatory inhalation and normal tidal breathing;
        responsive to the completion of the preparatory inhalation, control the pressure generator to maintain a pressure level of the pressurized flow of breathable gas below ambient air pressure immediately prior to an exsufflation;
        determine, based on the output signals from the one or more sensors, whether a gas parameter related to breathable gas expired by the subject breaches a threshold level before the exsufflation; and
        responsive to the gas parameter breaching the threshold level, further adjust the pressure level during the exsufflation to enhance secretion removal during the exsufflation.

2. The system of claim 1, wherein the one or more processors is configured to
    control the pressure generator to provide the pressurized flow of breathable gas at a first negative pressure level immediately prior to the exsufflation, and
    adjust the first negative pressure level based on the output signals to enhance secretion removal during the exsufflation.

3. The system of claim 2, wherein the output signals convey information related to a volume of gas expired by the subject while the pressurized flow of breathable gas is at the first negative pressure level before the exsufflation, and wherein the one or more processors adjusts the first negative pressure level responsive to the volume of gas expired by the subject breaching a threshold level before the exsufflation.

4. The system of claim 1, further comprising a user control interface, configured such that information indicating whether the subject is ready for the exsufflation comprises an input by the subject to the user control interface, wherein, responsive to receiving an indication of exsufflation readiness by the subject, the one or more processors control module is configured to control the pressure generator to generate the pressurized flow of breathable gas at a first negative pressure level immediately prior to the exsufflation and a second negative pressure level for delivery to the airway of the subject during the exsufflation.

5. The system of claim 1, wherein controlling the pressure generator to maintain a pressure level of the pressurized flow of breathable gas below ambient air pressure immediately prior to the exsufflation reduces a cross-sectional area of the airway of the subject from a current cross-sectional area.

6. A method to enhance secretion removal from an airway of a subject with a secretion removal enhancement system, the system comprising a pressure generator, one or more processors, and one or more sensors configured to generate output signals conveying information related to one or more gas parameters of the pressurized flow of breathable gas the method comprising:
    generating a pressurized flow of breathable gas for delivery to the airway of the subject with the pressure generator;
    detecting completion of a preparatory inhalation based on a comparison between the one or more gas parameters associated with the preparatory inhalation and normal tidal breathing;
    responsive to the completion of the preparatory inhalation, controlling the pressure generator to maintain a pressure level of the pressurized flow of breathable gas below ambient air pressure immediately prior to an exsufflation;
    determining, based on the output signals from the one or more sensors, whether a gas parameter related to breathable gas expired by the subject breaches a threshold level before the exsufflation; and
    responsive to the gas parameter breaching the threshold level, adjusting the pressure level during the exsufflation to enhance secretion removal during the exsufflation.

7. The method of claim 6, wherein the method further comprises:
    generating the output signals conveying information related to one or more gas parameters of the pressurized flow of breathable gas with the one or more sensors;
    controlling the pressure generator to provide the pressurized flow of breathable gas at a first negative pressure level immediately prior to the exsufflation; and
    adjusting the first negative pressure level based on the output signals to enhance secretion removal during the exsufflation.

8. The method of claim 7, wherein the output signals convey information related to a volume of gas expired by the subject while the pressurized flow of breathable gas is at the first negative pressure level before the exsufflation, and wherein the first negative pressure level is adjusted responsive to the volume of gas expired by the subject breaching a threshold level before the exsufflation.

9. The method of claim 6, wherein the method further comprises:
    receiving information indicating whether the subject is ready for the exsufflation via a user control interface; and
    responsive to receiving an indication of exsufflation readiness by the subject, controlling the pressure generator to generate the pressurized flow of breathable gas at a first negative pressure level immediately prior to the exsufflation and to generate the pressurized flow of breathable gas at a second negative pressure level for delivery to the airway of the subject during the exsufflation.

10. The method of claim 6, wherein controlling the pressure generator to maintain a pressure level of the pressurized flow of breathable gas below ambient air pressure immediately prior to the exsufflation reduces a cross-sectional area of the airway of the subject from a current cross-sectional area.

11. A system for enhancing secretion removal from an airway of a subject, the system comprising:
    means for generating a pressurized flow of breathable gas for delivery to the airway of the subject;
    means for generating output signals conveying information related to one or more gas parameters of the pressurized flow of breathable gas; and
    means for executing computer program modules, the computer program modules comprising:
        means for detecting completion of a preparatory inhalation based on a comparison between the one or more gas parameters associated with the preparatory inhalation and normal tidal breathing;
        responsive to the completion of the preparatory inhalation, means for controlling the means for generating the pressurized flow of breathable gas to maintain a pressure level of the pressurized flow of breathable gas below ambient air pressure immediately prior to an exsufflation;
        means for determining, based on the output signals, whether a gas parameter related to breathable gas expired by the subject breaches a threshold level before the exsufflation; and
        means for adjusting the pressure level before the exsufflation responsive to a gas parameter related to the breathable gas expired by the subject breaching a threshold level before the exsufflation.

12. The system of claim 11, wherein the means for controlling is configured to control the means for generating the pressurized flow of breathable gas to provide the pressurized flow of breathable gas at a first negative pressure level immediately prior to the exsufflation, and wherein the means for adjusting the first negative pressure level based on the output signals to enhance secretion removal during the exsufflation.

13. The system of claim 12, wherein the output signals convey information related to a volume of gas expired by the subject while the pressurized flow of breathable gas is at the first negative pressure level before the exsufflation, and wherein the means for adjusting adjusts the first negative pressure level responsive to the volume of gas expired by the subject breaching a threshold level before the exsufflation.

14. The system of claim 11, further comprising means for receiving information indicating whether the subject is ready for the exsufflation, wherein, responsive to receiving an indication of exsufflation readiness by the subject, the means for controlling is configured to control the means for generating the pressurized flow of breathable gas to generate the pressurized flow of breathable gas at a first negative pressure level immediately prior to the exsufflation and to generate the pressurized flow of breathable gas at a second negative pressure level for delivery to the airway of the subject during the exsufflation.

15. The system of claim 11, wherein controlling the means to generate the pressurized flow of breathable gas to maintain a pressure level of the pressurized flow of breathable gas below ambient air pressure immediately prior to the exsufflation reduces a cross-sectional area of the airway of the subject from a current cross-sectional area.

16. A method to enhance secretion removal from an airway of a subject with a secretion removal enhancement system, the system comprising a pressure generator, one or more sensors, and one or more processors, the one or more processors configured to execute computer program modules, the method comprising:
　generating a pressurized flow of breathable gas for delivery to the airway of the subject with the pressure generator;
　generating one or more output signals conveying information related to one or more gas parameters of the pressurized flow of breathable gas with the one or more sensors;
　detecting completion of a preparatory inhalation based on a comparison between a preparatory inhalation volume of breathable gas with a normal tidal breathing volume of breathable gas of the subject;
　controlling the pressure generator with the control module to maintain a pressure level of the pressurized flow of breathable gas below ambient air pressure immediately prior to an exsufflation, the controlling responsive to detecting completion of the preparatory inhalation;
　determining, based on the output signals from the one or more sensors, whether a gas parameter related to breathable gas expired by the subject breaches a threshold level before the exsufflation; and
　responsive to the gas parameter breaching the threshold level, further adjust the pressure level during the exsufflation to enhance secretion removal during the exsufflation.

17. A method to enhance secretion removal from an airway of a subject with a secretion removal enhancement system, the system comprising a pressure generator, one or more sensors, and one or more processors, the one or more processors configured to execute computer program modules, the computer program modules including a parameter module and a control module, the method comprising:
　generating a pressurized flow of breathable gas for delivery to the airway of the subject with the pressure generator;
　generating one or more output signals conveying information related to one or more gas parameters of the pressurized flow of breathable gas with the one or more sensors;
　detecting completion of a preparatory inhalation based on the output signals with the parameter module, the preparatory inhalation comprises an inhalation by the subject prior to an exsufflation, and wherein detecting completion of a preparatory inhalation comprises:
　　detecting a tidal breathing volume during a first period of time during normal tidal breathing of the subject;
　　determining a maximum tidal breathing volume change set point based on the normal tidal breathing of the subject during the first period of time;
　　detecting tidal breathing volume changes during a second period of time;
　　determining that an instance of a tidal breathing volume change during the second period of time breaches a threshold level above the maximum tidal breathing volume change set point; and
　　determining a tidal flow rate to be substantially zero, the substantially zero tidal flow rate determined just after determining the instance of the tidal breathing volume change breached the threshold level, the substantially zero tidal flow rate determination indicating completion of the preparatory inhalation; and
　controlling the pressure generator with the control module to maintain a pressure level of the pressurized flow of breathable gas below ambient air pressure immediately prior to an exsufflation, the controlling responsive to detecting completion of the preparatory inhalation.

18. The method of claim 16, further comprising determining an airway pressure level with the parameter module and controlling the pressure generator to provide a pressure level of the pressurized flow of breathable gas below ambient air pressure until the airway pressure level reaches the provided pressure level.

19. The method of claim 18, wherein the system further comprises a user control interface, and wherein the method further comprises responsive to the airway pressure level reaching a provided pressure level, controlling the user interface with the control module to generate an indication to the user that the airway pressure level has reached the provided pressure level and the system is ready for exsufflation.

20. The method of claim 16, wherein the method further comprises:
　controlling the pressure generator to provide the pressurized flow of breathable gas at a first negative pressure level immediately prior to the exsufflation; and
　adjusting the first negative pressure level based on the output signals to enhance secretion removal during the exsufflation.

21. The system of claim 1, wherein the one or more processors is configured to detect completion of the preparatory inhalation based on the comparison between a preparatory inhalation volume of breathable gas with a normal tidal breathing volume of breathable gas of the subject.

* * * * *